United States Patent [19]
DeSimone et al.

[11] Patent Number: 5,637,725
[45] Date of Patent: Jun. 10, 1997

[54] SUBSTITUTED ARYL AND CYCLOALKYL IMIDAZOLONES; A NEW CLASS OF GABA BRAIN RECEPTOR LIGANDS

[75] Inventors: Robert W. DeSimone, Durham; Charles A. Blum, Guilford, both of Conn.

[73] Assignee: Neurogen Corporation, Branford, Conn.

[21] Appl. No.: 462,674

[22] Filed: Jun. 5, 1995

[51] Int. Cl.$^6$ .................................................. C07D 263/58
[52] U.S. Cl. .................. 548/222; 514/367; 514/375; 548/153; 548/179; 548/217; 548/218; 546/114; 546/115
[58] Field of Search ...................... 514/367, 375; 548/179, 217, 222

[56] References Cited

U.S. PATENT DOCUMENTS

| | | | |
|---|---|---|---|
| 3,499,875 | 3/1970 | Pietrusza et al. | 548/222 |
| 4,882,342 | 11/1989 | von Der Saal | 548/222 |
| 4,886,803 | 12/1989 | Sueda | 514/367 |
| 5,501,980 | 3/1996 | Katerinopoulos et al. | 548/215 |

OTHER PUBLICATIONS

Taniguchi et al. Chem. Pharm. Bull. vol. 42, No. 2 301–9 (1993).
Kuzmierkiewicz, Chem. Abstr. vol. 106 Entry 50163 (1985.

*Primary Examiner*—Donald G. Daus
*Attorney, Agent, or Firm*—John J. McDonnell; Steven J. Sarussi

[57] ABSTRACT

Disclosed are compounds of the formula:

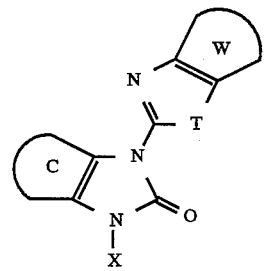

wherein:
T is NH, O, or S;
X is hydrogen, hydroxyl, lower alkyl, or an optionally substituted amide;
the W ring is an optionally substituted aryl or heteroaryl group; and

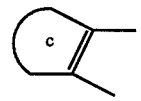

represents an optionally substituted benzo group or an optionally substituted 5, 6, 7, or 8 membered ring.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep and seizure disorders, overdose with benzodiazepine drugs and for enhancement of memory.

15 Claims, No Drawings

SUBSTITUTED ARYL AND CYCLOALKYL IMIDAZOLONES; A NEW CLASS OF GABA BRAIN RECEPTOR LIGANDS

BACKGROUND OF THE INVENTION

1. Field of the Invention

This invention relates to novel imidazolone derivatives which selectively bind to GABAa receptors. More specifically it relates to substituted aryl and cycloalkyl imidazolones and to pharmaceutical compositions comprising such compounds. It further relates to the use of such compounds in treating anxiety, sleep and seizure disorders, and overdoses of benzodiazepine-type drugs, and enhancing alertness.

2. Description of the Related Art

γ-Aminobutyric acid (GABA) is regarded as one of the major inhibitory amino acid transmitters in the mammalian brain. Over 40 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmakol. 258: 69–82). All subsequent electrophysiological studies (reviewed in Tallman et al. 1980, Science 207: 274–81, Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 249–60, Mohler & Okada, 1977, Science 198: 854–51, Mohler & Okada, 1977, Br. J. Psychiatry 133: 261–68). The average therapeutic doses of these drugs in man also correlate with receptor potency (Tallman et al. 1980, Science 207: 274–281).

In 1978, it became clear that GABA and related analogs could interact at the low affinity (1 mM) GABA binding site to enhance the binding of benzodiazepines to the clonazepam-sensitive site (Tallman et al. 1978, Nature, 274: 383–85). This enhancement was caused by an increase in the affinity of the benzodiazepine binding site due to occupancy of the GABA site. This data was interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274: 383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma. Biochem. Behav. 10: 825–30, Klepner et al. 1979, Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther.212: 337–46, Young et al., 1981 J. Pharmacol Exp. ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites has been demonstrated by Sieghart & Karobath, 1980, Nature 286: 285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into $\alpha$, $\beta$, $\gamma$, $\delta$, $\epsilon$, and provide a molecular basis for the GABAa receptor heterogeneity and distinctive regional pharmacology (Shivvers et al., 1980; Levitan et al., 1989). The $\gamma$ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predictive about the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen & Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazodiazepine (Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. I. Clin. Pharmacol. 1-4: 569–70). When a radiolabeled form of this compound was studied (Mohler & Richards, 1981, Nature 294: 763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous.

A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85, Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA (Braestrup & Nielson 1981, Nature 294: 472–474). Thus, the GABA shift predicts generally the expected behavioral properties of the compounds.

Various compounds have been prepared as benzodiazepine agonists and antagonists. For Example, U.S. Pat. Nos. 3,455,943, 4,435,403, 4,596,808, 4,623,649, and 4,719,210, German Patent No. DE 3,246,932, and Liebigs Ann. Chem. 1986, 1749 teach assorted benzodiazepine agonists and antagonists and related anti-depressant and central nervous system active compounds. U.S. Pat. No. 3,455,943 discloses compounds of the formula:

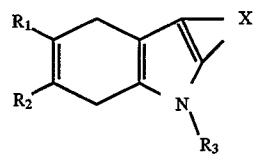

wherein $R_1$ is a member of the group consisting of hydrogen and lower alkoxy; $R_2$ is a member of the group consisting of hydrogen and lower alkoxy; $R_3$ is a member of the group consisting of hydrogen and lower alkyl; and X is a divalent radical selected from the group consisting of

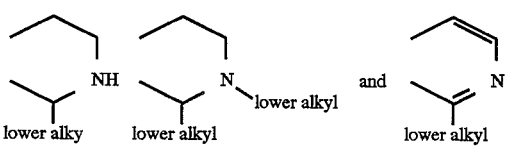

and the non-toxic acid addition salts thereof.

U.S. Pat. No. 4,435,403 teaches compounds of the formula:

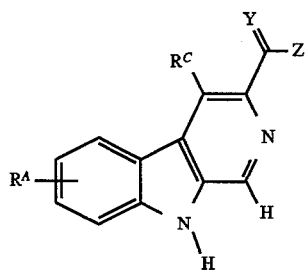

wherein $R^C$ is hydrogen, lower alkyl, alkoxyalkyl of up to 6 C-atoms, cycloalkyl of 3–6 C-atoms, arylalkyl of up to 8 C-atoms, or $(CH2)_nOR_2$ wherein $R_{20}$ is alkyl of up to 6 C-atoms, cycloalkyl of 3–6 C-atoms or arylalkyl of up to 8 C-atoms and n is an integer of 1 to 3; Y is oxygen, two hydrogen atoms or $NOR_1$, wherein $R_1$ is hydrogen, lower alkyl, aryl or arylalkyl of up to 6 C-atoms, $COR_2$, wherein $R_2$ is lower alkyl of up to 6 C-atoms, or Y is $CHCOOR_3$, wherein $R_3$ is hydrogen or lower alkyl or Y is $NNR_4R_5$, wherein $R_4$ and $R_5$ can be the same or different and each is hydrogen, lower alkyl, $C_{6-10}$-aryl, $C_{7-10}$-arylalkyl or $CONR_6R_7$, wherein $R_6$ and $R_7$ can be the same or different and each is hydrogen or lower alkyl or $R_4$ and $R_5$ together with the connecting N-atom, form a 5- or 6-membered heterocyclic ring which optionally may also contain an O-atom or up to 3 N-atoms and which optionally may be substituted by a lower alkyl group; Z is hydrogen, or alkoxy or aralkoxy each of up to 10 C-atoms and each optionally substituted by hydroxy, or Z is alkyl of up to 6 C-atoms, $C_{6-10}$-aryl or $C_{7-10}$-arylalkyl each of which may optionally be substituted by a $COOR_8$ or a $CONR_9R_{10}$ group, wherein $R_8$ is alkyl of up to 6 C-atoms, and $R_9$ and $R_{10}$ can be the same or different and each is hydrogen or alkyl of up to 6 C-atoms; or Z is $NR_9R_{10}$, wherein $R_9$ and $R_{10}$ are as defined above; or Z is $NR_{11}CHR_{12}R_{13}$, wherein $R_{11}$ and $R_{12}$ each is hydrogen or together form a N=C double bond, wherein $R_{13}$ is $C_{1-10}$-alkyl or $NR_{14}R_{15}$, wherein $R_{14}$ and $R_{15}$ are the same or different and each is hydrogen, OH or alkyl or alkoxy each of up to 6 C-atoms, or wherein $R_{12}$ and $R_{13}$ together are oxygen, in which case, $R_{11}$ is hydrogen; or Z is $COOR_2$ wherein $R_2$ is as defined above; or Y and Z, together with the connecting C-atom, may form a 5- or 6-membered heterocyclic ring which contains an O-atom, adjoining O- and N-atoms or up to 4 N atoms and which optionally may be substituted by a lower alkyl group, hydroxy or oxo.

U.S. Pat. No. 4,596,808 discloses compounds of the formula:

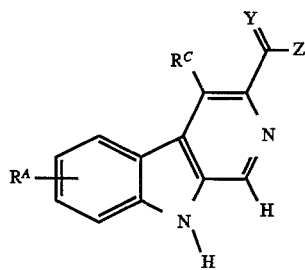

wherein $R^A$ is H, F, Cl, Br, I, $NO_2$, CN, $CH_3$, $CF_3$, $SCH_3$, $NR_{16}R_{17}$ or $NHCOR_{16}$, wherein $R_{16}$ of $R_{17}$ are the same or different and each is hydrogen or alkyl, alkenyl or alkynyl each of up to 6 C-atoms, arylalkyl or cycloalkyl each of up to 10 C-atoms, or wherein $R_{16}$ and $R_{17}$ together form a saturated or unsaturated 3–7 membered heterocyclic ring.

U.S. Pat. No. 4,623,649 teaches compounds of the formula:

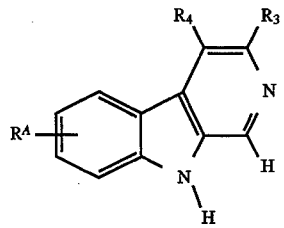

wherein $R_3$ is an oxadiazolyl residue of the formula

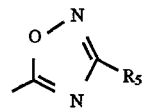

wherein $R_5$ stands for lower alkyl of up to 3 carbon atoms or an ester —$CO_2R_6$ with $R_6$ being hydrogen or lower alkyl of up to 3 carbon atoms, $R_4$ is hydrogen, lower alkyl of up to 3 carbon atoms, or $CH_2OR_9$ wherein $R_9$ is lower alkyl of up to 3 carbon atoms, $R^A$ is phenyl or a hydrocarbon residue containing 2–10 carbon atoms which can be cyclic or acyclic, saturated or unsaturated, branched or unbranched, and which can optionally be substituted by oxo, formyl OH, O-alkyl of up to 3 carbon atoms or phenyl, and wherein in a cyclic hydrocarbon residue, a $CH_2$-group can be replaced by oxygen.

U.S. Pat. No. 4,719,210 discloses compounds of the formula:

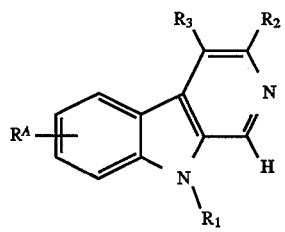

wherein $R_1$ is hydrogen or a protecting group, $R_2$ is —CH=$CR_4$ or —C=$CR_4$, $R_4$ is hydrogen or halogen, $R_3$ is hydrogen, lower alkyl or lower alkoxyalkyl, $R^A$ is, inter alia, hydrogen, $OR_7$, lower alkyl, which optionally is substituted with aryl, lower alkoxy or $NR_5R_6$, $R_5$ and $R_6$ can be the same or different and in each case is hydrogen, lower alkyl or together with the nitrogen atom a 5–6 member ring, which can contain another heteroatom. $R_7$ is lower alkyl, optionally substituted aryl or arylalkyl, and each compound can contain one or more $R^A$ radicals which are not hydrogen.

These compounds differ from the compounds of the present invention. These U.S. Patents teach carbocyclic compounds having pyridine or piperidine rings but lack the imidazolone ring present in the compounds of the present invention.

German Patent No. DE 3,246,932 discloses compounds of the formula:

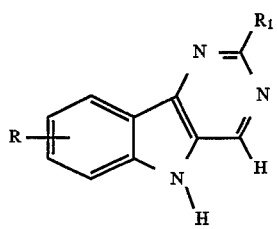

wherein R=halogen, $NO_2$, $CO_2H$, modified $CO_2H$, $R_2O$, $R_2S(O)_n$; n=0–2; and $R_1$=H, alkyl, cycloalkyl, arylalkyl, aryl, $CO_2H$, amino $R_2O$, $R_2S(0)_n$. However no examples were exemplified in this patent with $R_1$=aryl.

Liebigs Ann. Chem. 1986, 1749–1764 teaches compounds of the formula:

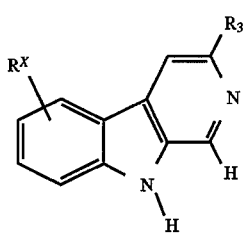

where $R^x$ is hydrogen, methyl, benzyloxy, or methoxy, and $R_3$ is carboethoxy.

Japanese Patent No JP 57149277 describes a compound of the formula:

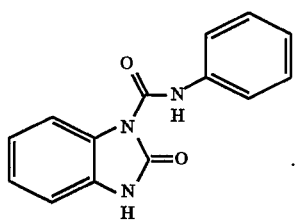

Meanwell et al, *J. Org. Chem.*: 60, 1565–1582 (1995) discloses compounds of the following formula

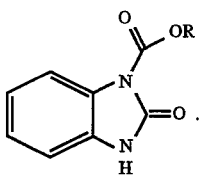

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, sleep, and seizure disorders, overdose with benzodiazepine drugs and for enhancement of memory. Accordingly, a broad embodiment of the invention is directed to compounds of Formula I:

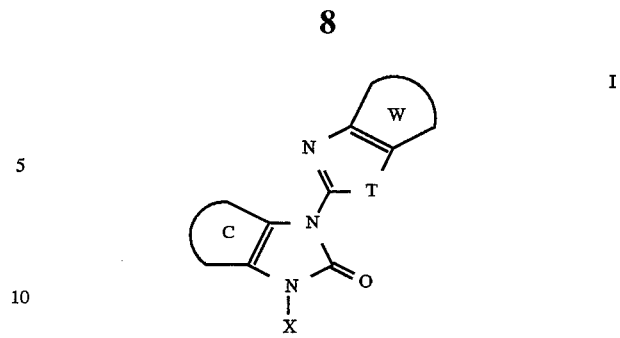

wherein:

T is NH, O, or S;

X is hydrogen, hydroxyl, lower alkyl, or $CONR_1R_2$ where $R_1$ and $R_2$ independently represent hydrogen or lower alkyl;

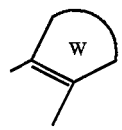

represents benzo, thieno, or pyrido, each of which is optionally mono or disubstituted with halogen, hydroxyl, lower alkyl, amino, mono- or dialkylamino where each alkyl is lower alkyl, or lower alkoxy; and

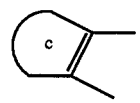

represents

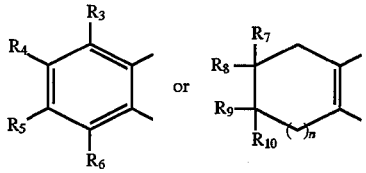

wherein:

n is 0, 1, 2, or 3;

$R_3$, $R_4$, $R_5$ and $R_6$ are the same or different and represent hydrogen, halogen, lower alkyl, lower alkoxy, phenyl, or 2-, 3-, or 4-pyridyl; or phenylalkyl or 2-, 3-, or 4-pyridylalkyl where each alkyl is lower alkyl, each of which is mono or disubstituted with halogen, hydroxyl, lower alkyl or alkoxy lower alkyl; and $R_7$, $R_8$, $R_9$, $R_{10}$ independently represents hydrogen, lower alkyl; or $R_7$ and $R_8$ together may represent a group of the formula

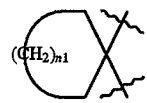

where n1 is 0, 1, 2.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep and seizure disorders, overdose with benzodiazepine drugs and for enhancement of memory.

DETAILED DESCRIPTION OF THE INVENTION

The novel compounds encompassed by the instant invention can be described by the following general formula I:

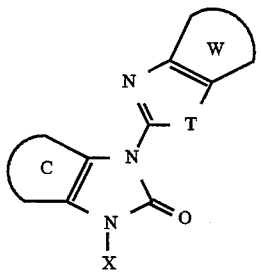
I wherein:

T is NH, O, or S;

X is hydrogen, hydroxyl, lower alkyl, or CONR₁R₂ where R₁ and R₂ independently represent hydrogen or lower alkyl;

represents benzo, thieno, or pyrido, each of which is optionally mono or disubstituted with halogen, hydroxyl, lower alkyl, amino, mono- or dialkylamino where each alkyl is lower alkyl, or lower alkoxy;

represents

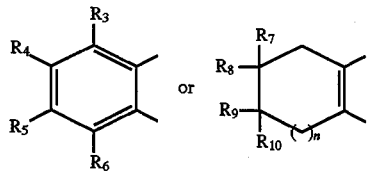

wherein:

n is 0, 1, 2, or 3;

R₃, R₄, R₅ and R₆ are the same or different and represent hydrogen, halogen, lower alkyl, lower alkoxy, phenyl, or 2-, 3-, or 4-pyridyl; phenylalkyl or 2-, 3-, or 4-pyridylalkyl where each alkyl is lower alkyl, each of which is mono or disubstituted with halogen, hydroxyl, lower alkyl or alkoxy lower alkyl;

R₇, R₈, R₉, R₁₀ independently represents hydrogen, lower alkyl; or

R₇ and R₈ together may represent a group of the formula

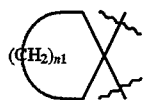

where n1 is 0, 1, 2.

In addition, the present invention encompasses compounds of the Formula II.

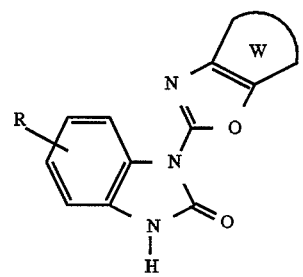
II wherein:

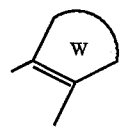

(the "W ring") represents benzo, thieno, or pyrido, each of which is optionally mono or disubstituted with halogen, hydroxyl, lower alkyl, lower alkoxy, amino, or mono- or dialkylamino where each alkyl is lower alkyl; and R is hydrogen, halogen, lower alkyl, lower alkoxy, or hydroxy.

Preferred compounds of Formula II are those where the W ring is benzo or pyrido, each of which is mono or disubstituted with halogen, hydroxyl, lower alkyl, lower alkoxy, amino, or mono- or dialkylamino where each alkyl is lower alkyl. More preferred compounds of Formula II are those where R is hydrogen or halogen; and the W ring is benzo or pyrido, each of which is mono or disubstituted with halogen, hydroxyl, lower alkyl, lower alkoxy, amino, or mono- or dialkylamino where each alkyl is lower alkyl.

In addition, the present invention encompasses compounds of the Formula III.

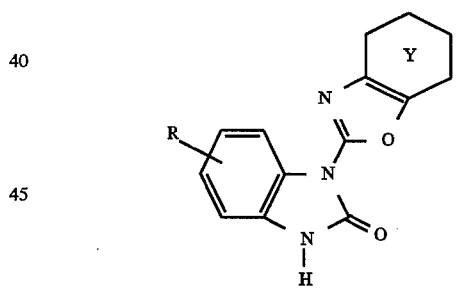
III wherein:

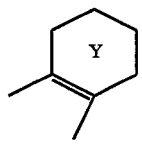

(the "Y ring") represents benzo or pyrido, each of which is optionally mono or disubstituted with halogen, hydroxyl, lower alkyl, lower alkoxy, amino, or mono- or dialkylamino where each alkyl is lower alkyl; and R is hydrogen, halogen, lower alkyl, lower alkoxy, or hydroxy.

Preferred compounds of Formula III are those where the Y ring is benzo or pyrido, each of which is mono or disubstituted with halogen, hydroxyl, lower alkyl, lower alkoxy, amino, or mono- or dialkylamino where each alkyl is lower alkyl. More preferred compounds of Formula III are those where R is hydrogen or halogen; and the Y ring is benzo or pyrido each of which is mono or disubstituted with halogen, hydroxyl, lower alkyl, lower alkoxy, amino, or mono- or dialkylamino where each alkyl is lower alkyl.

In addition, the present invention encompasses compounds of the Formula IV.

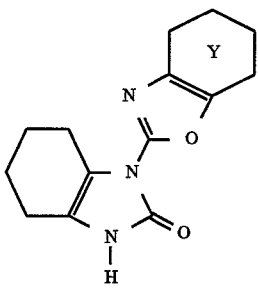

wherein:

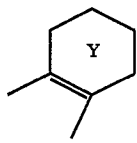

represents benzo or pyrido, each of which is optionally mono or disubstituted with halogen, hydroxyl, lower alkyl, lower alkoxy, amino, or mono- or dialkylamino where each alkyl is lower alkyl.

Preferred compounds of Formula IV are those where the Y ring is benzo or pyrido, each of which is mono or disubstituted with halogen, hydroxyl, lower alkyl, lower alkoxy, amino, or mono- or dialkylamino where each alkyl is lower alkyl. More preferred compounds of Formula IV are those where the Y ring is benzo or pyrido, each of which is mono or disubstituted with halogen, hydroxyl, lower alkyl, lower alkoxy, amino, or mono- or dialkylamino where each alkyl is lower alkyl.

In addition, the present invention encompasses compounds of the Formula V

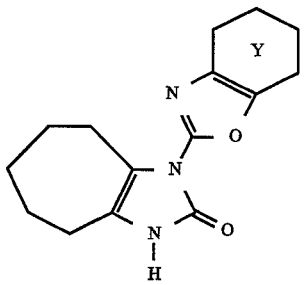

wherein:

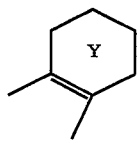

represents benzo or pyrido, each of which is optionally mono or disubstituted with halogen, hydroxyl, lower alkyl, lower alkoxy, amino, or mono- or dialkylamino where each alkyl is lower alkyl.

Preferred compounds of Formula V are those where the Y ring is benzo or pyrido, each of which is mono or disubstituted with halogen, hydroxyl, lower alkyl, lower alkoxy, amino, or mono- or dialkylamino where each alkyl is lower alkyl. More preferred compounds of Formula V are those where the Y ring is benzo or pyrido, each of which is mono or disubstituted with halogen, hydroxyl, lower alkyl, lower alkoxy, amino, or mono- or dialkylamino where each alkyl is lower alkyl.

The system used herein for numbering the imidazo portion of the compounds of Formulae III–V is as follows:

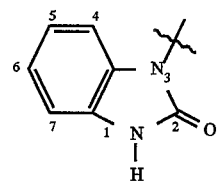

The system used herein for numbering the oxazyl portion of the compounds of Formulae III–V is as follows:

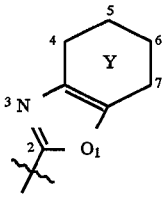

Representative compounds of the present invention, which are encompassed by Formula I, include, but are not limited to the compounds shown below in Table 1 and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which can be employed to prepare non-toxic pharmaceutically acceptable addition salts and acylated prodrugs of the compounds encompassed by Formula I.

By benzo as used herein is meant a group of the formula

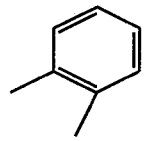

optionally substituted with up to two groups selected from halogen, hydroxyl, lower alkyl, amino, mono- or dialkylamino where each alkyl is lower alkyl, or lower alkoxy.

By thieno as used herein is meant a group of the formula

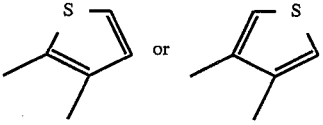

optionally substituted with up to two groups selected from halogen, hydroxyl, lower alkyl, amino, mono- or dialkylamino where each alkyl is lower alkyl, or lower alkoxy.

By pyrido as used herein is meant a group of the formula

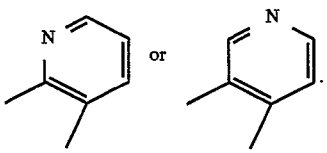

optionally substituted with up to two groups selected from halogen, hydroxyl, lower alkyl, amino, mono- or dialkylamino where each alkyl is lower alkyl, or lower alkoxy.

By lower alkyl in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By lower alkoxy in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By halogen in the present invention is meant fluorine, bromine, chlorine, and iodine.

By N-alkylpiperazyl in the invention is meant radicals of the formula:

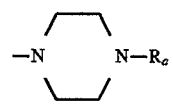

where $R_a$ is lower alkyl as defined above.

Representative imidazolone derivatives according to the invention are shown in Table 1 below.

TABLE 1[1]

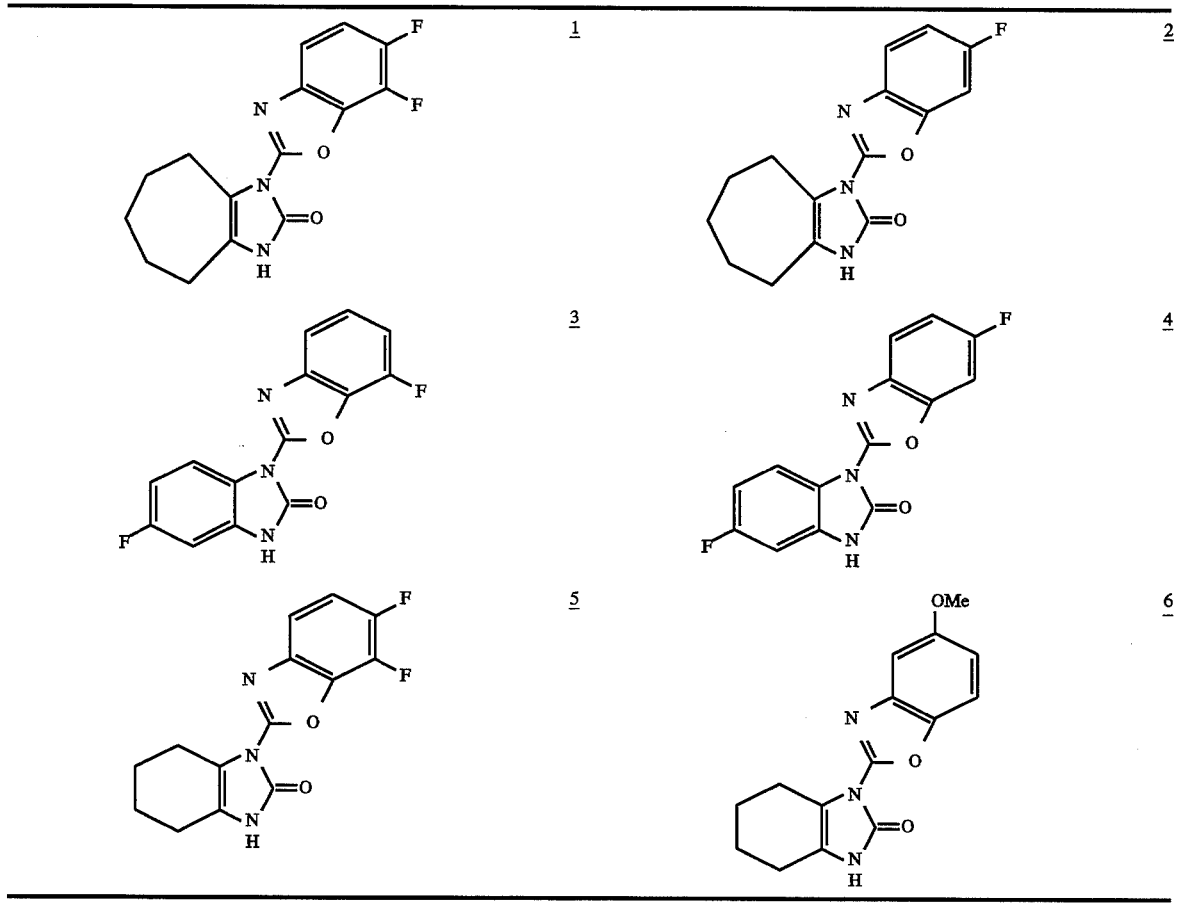

The number below each compound is its compound number.

The pharmaceutical utility of compounds of this invention are indicated by the following assay for GABAa receptor activity.

Assays are carried out as described in Thomas and Tallman (J. Bio. Chem. 156: 9838–9842, J. Neurosci. 3: 433–440, 1983). Rat cortical tissue is dissected and homogenized in 25 volumes (w/v) of 0.05M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to a form for the calculation of IC$_{50}$ and Hill Coefficient (nH). Data for compounds of this invention are listed in Table 2.

TABLE 2

| Compound Number[1] | Ki(nm) |
|---|---|
| 1 | 3.0 |
| 2 | 4.6 |
| 3 | 14 |
| 4 | 5 |
| 5 | 21 |
| 6 | 81 |

[1]Compound numbers relate to compounds shown in Table 1.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Representative methods for the preparation of compounds of the present invention are shown in Schemes I–IV.

Scheme I:

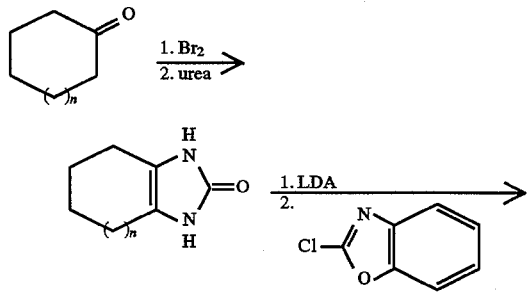

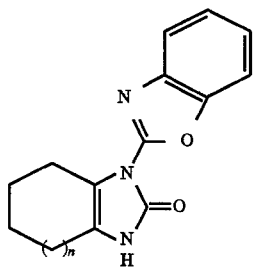

A procedure for the preparation of the tetrahydrobenzimidazolone is described by Zav'yalov et al. in Chem Heterocycl. Compd.(Engl. Transl.), 26:708 (1990).

Scheme II:

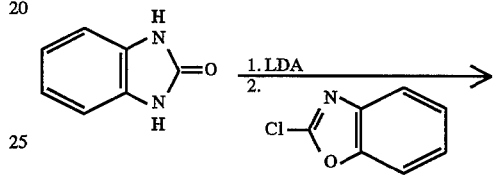

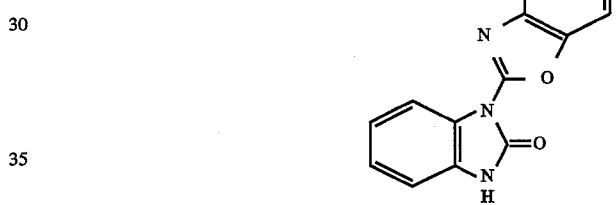

Scheme III:

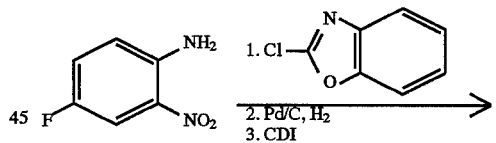

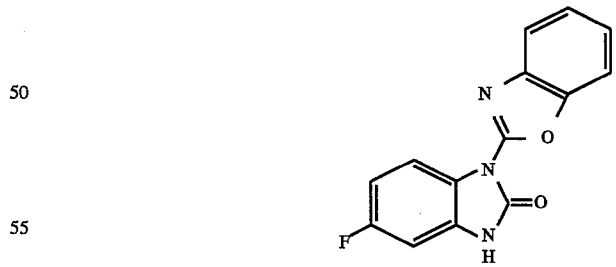

Scheme IV:

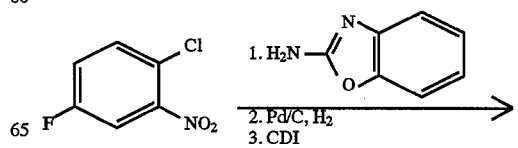

-continued
Scheme IV:

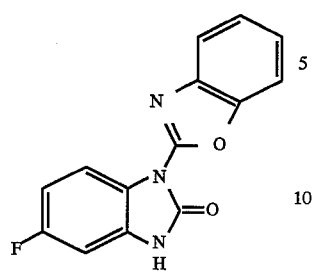

As it is used in the above schemes, CDI means carbonyl di-imidazole.

The invention is further illustrated by the following examples which are not to be construed as limiting the invention in scope or spirit to the specific procedures and compounds described therein.

EXAMPLE 1

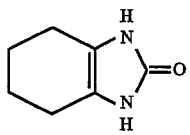

A mixture of 2-bromocyclohexanone (6.23 g, 0.035 mol) and urea (2.1 g, 0.035 mol) is refluxed in a solution of ammonium acetate (10 g), acetic acid (15 mL) and water (50 mL) for 4 h. Upon cooling slowly to room temp, white crystals form in the reaction vessel. The solid is collected by suction filtration, washed thoroughly with water and ether, and dried in vacuo to afford 4,5,6,7-tetrahydro-2-benzimidazolone (Compound 7).

EXAMPLE 2

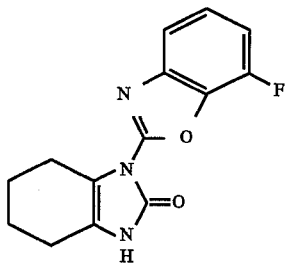

To a suspension of 4,5,6,7-tetrahydro-2-benzimidazolone (0.358 g, 2.595 mmol) in dry THF is added Lithium diisopropyl amide (1.5M solution in cyclohexane) dropwise at room temperature. The resulting homogeneous solution is stirred for 10 minutes at room temperature and then 2-chloro-7-fluoro-benzoxazole (0.445 g, 2.595mmol) in THF is added at a moderate rate via syringe. After stirring at room temperature for 1 h, water is added to the reaction vessel and the THF is removed under reduced pressure. The resulting solid is collected via suction filtration and washed successively with water, methanol and ether to afford 3-(2-(7-fluorobenzoxazyl)-4,5,6,7-tetrahydrobenzimidazol-2-(1H)-one; (Compound 8); mp 250°–253° C. as a pale yellow solid.

EXAMPLE 3

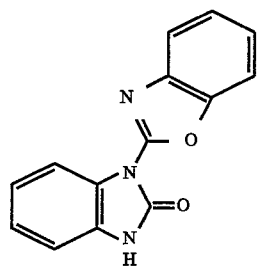

To a suspension of 2-hydroxybenzimidazole (0.134 g, 1.0 mmole) in dry DMF is added NaH, (45 mg, 1.1 mmole) at room temperature. The resulting homogeneous solution is stirred for 10 minutes at room temperature and then 2-chlorobenzoxazole (0.12 mL, 1.0 mmole) is added at a moderate rate via syringe. After stirring at room temperature for 1 h, water is added to the reaction vessel and the resulting solid is collected via suction filtration and washed successively with water, methanol and ether to afford 3-(2-benzoxazyl)-benzimidazol-2-(1H)-one; (Compound 9); mp 245°–246° C. as a pale white solid.

EXAMPLE 4

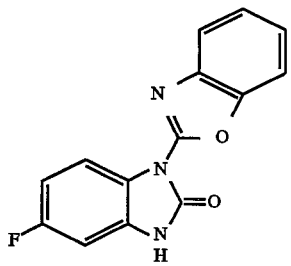

To a solution of (0.3 g, 1.9 mmole) of 4-fluoro-2-nitroaniline and (2.62 g, 0.019 mole) of $K_2CO_3$ in dry DMF is added (0.23 mL, 2.09 mmole) of 2-chlorobenzoxazole at a moderate rate via syringe. After stirring at room temperature for 12 h, water is added to the reaction vessel and the resulting solid is collected via suction filtration and washed with water. The solid is then taken up in EtOAc, dried over anhydrous $MgSO_4$, filtered and solvent removed under reduced pressure. The resulting 4-fluoro-2-nitro-(2-benzoxazyl)-1-aniline is treated at 40 psi with $H_2$ over 10% Pd/C in EtOH for 1 hr. The resulting mixture is filtered through Celite, washed with EtOH, and solvent removed under reduced pressure.

The resulting diamine is treated with 1,1'-Carbonyldiimidazole (CDI) at room temperature in dry DMF for 12 hr. Water is added, the resulting solid is collected via suction filtration and washed successively with water, methanol and ether to afford 3-(2-(benzoxazyl))-5-fluorobenzimidazol-2-(1H)-one; (Compound 10); mp 287°–288° C., as a pale yellow solid.

EXAMPLE 5

The following compounds are prepared essentially according to the procedures described in Examples 1–4, and as shown in Schemes 1–4:

(1) 3-(2-(5-fluorobenzoxazyl))-benzimidazol-2-(1H)-one; (Compound 11); mp: 400° C.

(2) 3-(2-(6-fluorobenzoxazyl))-benzimidazol-2-(1H)-one; (Compound 12); mp: 266°–268 C.

(3) 3-(2-(7-fluorobenzoxazyl))-benzimidazol-2-(1H)-one; (Compound 13); mp: 340°–345 C.

(4) 3-(2-(benzoxazyl))-6-fluorobenzimidazol-2-(1H)-one; (Compound 14); mp: 295°–296 C.

(5) 3-(2-(6-fluorobenzoxazyl))-6-fluorobenzimidazol-2-(1H)-one; (Compound: 4); mp 284°–285° C.

(6) 3-(2-(5-methoxybenzoxazyl))-benzimidazol-2-(1H)-one; (Compound 15); mp: 360°362° C.

(7) 3-(2-(6-methoxybenzoxazyl))-benzimidazol-2-(1H)-one; (Compound 16); mp: 365°367° C.

(8) 3-(2-(6,7-difluorobenzoxazyl))-benzimidazol-2-(1H)-one; (Compound 17); mp: 360°–362° C.

(9) 3-(2-(7-fluorobenzoxazyl))-6-fluorobenzimidazol-2-(1H)-one; (Compound 3); mp: 284°–285° C.

(10) 3-(2-(7-fluorobenzoxazyl))-5-fluorobenzimidazol-2-(1H)-one; (Compound 18); mp: 268°–270° C.

(11) 3-(2-(benzthiazyl))-benzimidazol-2-(1H)-one; (Compound 19); mp: 291°–293° C.

(12) 3-(2-benzoxazyl)-4,5,6,7-tetrahydrobenzimidazol-2-(1H)-one; (Compound 20); mp: 205°–205° C.

(13) 3-(2-(6-fluorobenzoxazyl)-,4,5,6,7-tetrahydrobenzimidazol-2-(1H)-one; (Compound 21); mp: 255°–258° C.

(14) 3-(2-(5-fluorobenzoxazyl)-1,4,5,6,7-tetrahydrobenzimidazol-2-(1H)-one; (Compound 22).

(15) 3-(2-(5-methoxybenzoxazyl)-,4,5,6,7-tetrahydrobenzimidazol-2-(1H)-one; (Compound 6); mp: 214°–217° C.

(16) 3-(2-(6,7-difluorobenzoxazyl)-,4,5,6,7-tetrahydrobenzimidazol-2-(1H)-one; (Compound 5); mp: 228°–23 1° C.

(17) 3-(2-(6-methoxybenzoxazyl)-,4,5,6,7-tetrahydrobenzimidazol-2-(1H)-one; (Compound 23); mp: 211°–214° C.

(18) 3-(2-benzoxazyl)-1,4,5,6,7,8-hexahydrocycloheptylimidazol-2-one; (Compound 24); mp: 164°–166° C.

(19) 3-(2-(6-fluorobenzoxazyl)- 1,4,5,6,7,8-hexahydrocycloheptylimidazol-2-one; (Compound 2); mp: 190°–192° C.

(20) 3-(2-(5-fluorobenzoxazyl)- 1,4,5,6,7,8-hexahydrocycloheptylimidazol-2-one; (Compound 25); mp: 206°–209° C.

(21) 3-(2-(7-fluorobenzoxazyl)- 1,4,5,6,7,8-hexahydrocycloheptylimidazol-2-one; (Compound 26); mp: 208°–210° C.

(22) 3-(2-(5-methoxybenzoxazyl)- 1,4,5,6,7,8-hexahydrocycloheptylimidazol-2-one; (Compound 27); mp: 225°–227° C.

(23) 3-(2-(6,7-difluorobenzoxazyl)-1,4,5,6,7,8-hexahydrocycloheptylimidazol-2-one; (Compound 1); mp: 204°–206° C.

(24) 3-(2-(6-methoxybenzoxazyl)- 1,4,5,6,7,8-hexahydrocycloheptylimidazol-2-one; (Compound 28); mp: 211°–213° C.

(25) 3-(2-(6-methylbenzoxazyl))-benzimidazol-2-(1H)-one; (Compound 29); mp: 350° C. (dec.).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

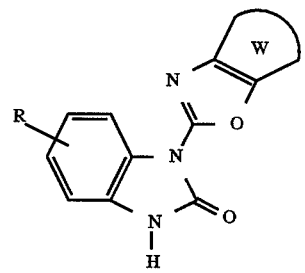

or the pharmaceutically acceptable non-toxic salts thereof wherein:

R represents R is hydrogen, halogen, lower alkyl, lower alkoxy, or hydroxy; and

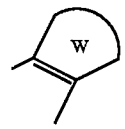

represents benzo unsubstituted, monosubstituted with lower alkyl, halogen or lower alkoxy, or mono- or disubstituted with halogen or lower alkoxy.

2. A compound according to claim 1, wherein the benzo group is 5-fluorobenzo, 6-fluorobenzo, 7-fluorobenzo, 5-methoxybenzo, 6-methoxybenzo, 6-methylbenzo, or 6,7-difluorobenzo.

3. A compound according to claim 1, which is 3-(2-benzoxazyl)-benzimidazol-2-(1H)-one.

4. A compound according to claim 1, which is 3-(2-(benzoxazyl))-5-fluorobenzimidazol-2-(1H)-one.

5. A compound according to claim 1, which is 3-(2-(5-fluorobenzoxazyl))-benzimidazol-2-(1H)-one.

6. A compound according to claim 1, which is 3-(2-(6-fluorobenzoxazyl))-benzimidazol-2-(1H)-one.

7. A compound according to claim 1, which is 3-(2-(7-fluorobenzoxazyl))-benzimidazol-2-(1H)-one.

8. A compound according to claim 1, which is 3-(2-(benzoxazyl))-6-fluorobenzimidazol-2-(1H)-one.

9. A compound according to claim 1, which is 3-(2-(6-fluorobenzoxazyl))-6-fluorobenzimidazol-2-(1H)-one.

10. A compound according to claim 1, which is 3-(2-(5-methoxybenzoxazyl))-benzimidazol-2-(1H)-one.

11. A compound according to claim 1, which is 3-(2-(6-methoxybenzoxazyl))-benzimidazol-2-(1H) -one.

12. A compound according to claim 1, which is 3-(2-(6,7-difluorobenzoxazyl))-benzimidazol-2-(1H)-one.

13. A compound according to claim 1, which is 3-(2-(7-fluorobenzoxazyl)) -6-fluorobenzimidazol-2-(1H)-one.

14. A compound according to claim 1, which is 3-(2-(7-fluorobenzoxazyl))-5-fluorobenzimidazol-2-(1H)-one.

15. A compound according to claim 1, which is 3-(2-(6-methylbenzoxazyl))-benzimidazol-2-(1H)-one.

* * * * *